(12) United States Patent
West

(10) Patent No.: US 6,447,732 B1
(45) Date of Patent: Sep. 10, 2002

(54) INCENSE BURNING ASSEMBLY

(76) Inventor: Vernon L. West, 1795 Elmore Ave., Columbus, OH (US) 43224

( * ) Notice: Subject to any disclaimer, the term of this patent is extended or adjusted under 35 U.S.C. 154(b) by 22 days.

(21) Appl. No.: 09/928,092

(22) Filed: Aug. 10, 2001

(51) Int. Cl.[7] ................................................. A61L 9/03
(52) U.S. Cl. ........................... 422/126; 422/5; 422/305; 422/306; 431/289
(58) Field of Search ................................ 422/126, 4, 5, 422/305, 306; 424/40, 76.1; 431/289

(56) References Cited

U.S. PATENT DOCUMENTS

| | | | |
|---|---|---|---|
| 3,175,876 A | * | 3/1965 | Fredricks ..................... 21/116 |
| 3,958,917 A | | 5/1976 | Naz |
| 4,347,217 A | * | 8/1982 | Radkins et al. ............. 422/126 |
| 5,690,484 A | | 11/1997 | Leonard et al. |
| D394,513 S | | 5/1998 | Davis |
| 5,871,553 A | | 2/1999 | Spaulding |
| 5,879,694 A | | 3/1999 | Morrison et al. |
| 6,036,925 A | | 3/2000 | Adams et al. |
| 6,086,853 A | * | 7/2000 | Michaels ..................... 424/40 |

* cited by examiner

Primary Examiner—Robert J. Warden, Sr.
Assistant Examiner—Sean E. Conley

(57) ABSTRACT

An incense burning assembly for allowing a user to easily distribute an agreeable scent throughout the home by burning incense without the messy ashes. The incense burning assembly includes a container. The container has an outer perimeter for defining an interior space. A holding member is positioned in the interior space. The holding member is structured to include a hole. The hole is adapted for receiving a portion of a stick of incense.

6 Claims, 1 Drawing Sheet

INCENSE BURNING ASSEMBLY

BACKGROUND OF THE INVENTION

1. Field of the Invention

The present invention relates to incense burning assemblies and more particularly pertains to a new incense burning assembly for allowing a user easily distribute an agreeable scent throughout the home by burning incense without the messy ashes.

2. Description of the Prior Art

The use of incense burning assemblies is known in the prior art. More specifically, incense burning assemblies heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,958,917; U.S. Pat. No. 5,871,553; U.S. Pat. No. 6,036,925; U.S. Pat. No. 5,879,694; U.S. Pat. No. 5,690,484; and U.S. Pat. No. Des. 394,513.

While these devices fulfill their respective, particular objectives and requirements, the aforementioned patents do not disclose a new incense burning assembly. The inventive device includes a container. The container has an outer perimeter for defining an interior space. A holding member is positioned in the interior space. The holding member is structured to include a hole. The hole is adapted for receiving a portion of a stick of incense.

In these respects, the incense burning assembly according to the present invention substantially departs from the conventional concepts and designs of the prior art, and in so doing provides an apparatus primarily developed for the purpose of allowing a user easily distribute an agreeable scent throughout the home by burning incense without the messy ashes.

SUMMARY OF THE INVENTION

In view of the foregoing disadvantages inherent in the known types of incense burning assemblies now present in the prior art, the present invention provides a new incense burning assembly construction wherein the same can be utilized for allowing a user easily distribute an agreeable scent throughout the home by burning incense without the messy ashes.

The general purpose of the present invention, which will be described subsequently in greater detail, is to provide a new incense burning assembly apparatus and method which has many of the advantages of the incense burning assemblies mentioned heretofore and many novel features that result in a new incense burning assembly which is not anticipated, rendered obvious, suggested, or even implied by any of the prior art incense burning assemblies, either alone or in any combination thereof.

To attain this, the present invention generally comprises a container. The container has an outer perimeter for defining an interior space. A holding member is positioned in the interior space. The holding member is structured to include a hole. The hole is adapted for receiving a portion of a stick of incense.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new incense burning assembly apparatus and method which has many of the advantages of the incense burning assemblies mentioned heretofore and many novel features that result in a new incense burning assembly which is not anticipated, rendered obvious, suggested, or even implied by any of the prior art incense burning assemblies, either alone or in any combination thereof.

It is another object of the present invention to provide a new incense burning assembly, which may be easily and efficiently manufactured and marketed.

It is a further object of the present invention to provide a new incense burning assembly, which is of a durable and reliable construction.

An even further object of the present invention is to provide a new incense burning assembly which is susceptible of a low cost of manufacture with regard to both materials and labor, and which accordingly is then susceptible of low prices of sale to the consuming public, thereby making such incense burning assembly economically available to the buying public.

Still yet another object of the present invention is to provide a new incense burning assembly, which provides in the apparatuses and methods of the prior art some of the advantages thereof, while simultaneously overcoming some of the disadvantages normally associated therewith.

Still another object of the present invention is to provide a new incense burning assembly for allowing a user easily distribute an agreeable scent throughout the home by burning incense without the messy ashes.

Yet another object of the present invention is to provide a new incense burning assembly, which includes a container. The container has an outer perimeter for defining an interior space. A holding member is positioned in the interior space.

The holding member is structured to include a hole. The hole is adapted for receiving a portion of a stick of incense.

Still yet another object of the present invention is to provide a new incense burning assembly that would allow the burning ashes to naturally and neatly fall into the bowl below during the burning process to eliminate scattered or blown ashes.

Even still another object of the present invention is to provide a new incense burning assembly that would be more environmentally safe than utilizing aerosol sprays, solid and plug-in room deodorizers.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
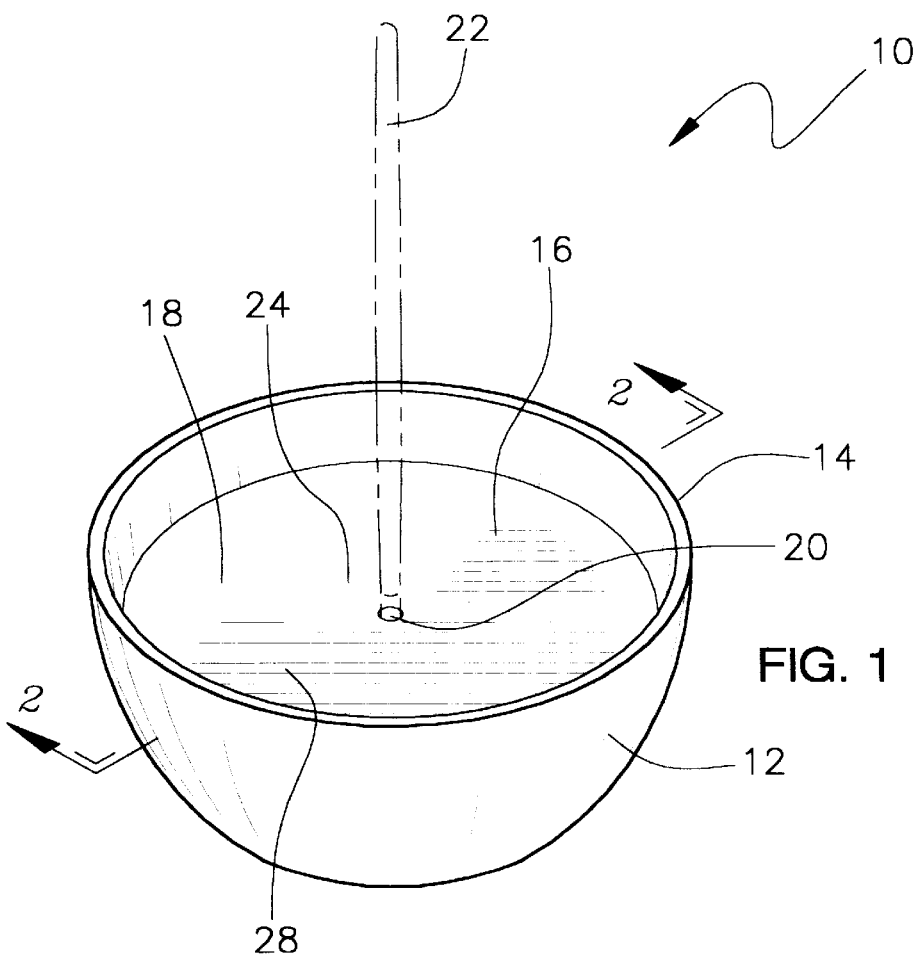
FIG. 1 is a perspective view of a new incense burning assembly according to the present invention.
Figure 2:
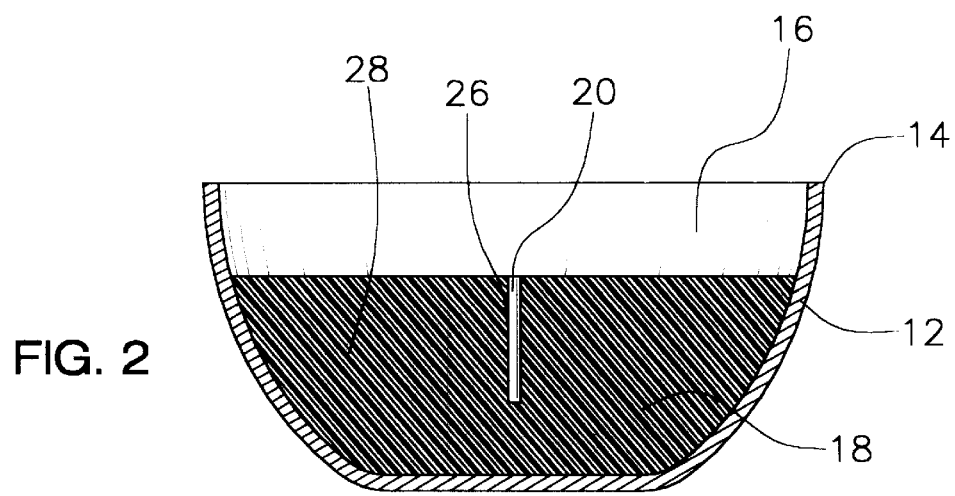
FIG. 2 is a cross-sectional view of the present invention.

With reference now to the drawings, and in particular to FIGS. 1 through 2 thereof, a new incense burning assembly embodying the principles and concepts of the present invention and generally designated by the reference numeral 10 will be described.

As best illustrated in FIGS. 1 through 2, the incense burning assembly 10 generally comprises a container 12. The container 12 has an outer perimeter 14 for defining an interior space 16. A holding member 18 is positioned in the interior space 16. The holding member 18 is structured to include a hole 20. The hole 20 is adapted for receiving a portion of a stick of incense 22.

The hole 20 is positioned proximate a center 24 of the holding member 18 such that the stick of incense 22 is positioned in a substantially central position relative to the container 12. The hole 20 is formed by a perimeter wall 26. The perimeter wall 26 is substantially vertically oriented when the container 12 is positioned on a support surface whereby the stick of incense 22 is held in a substantially vertical orientation when inserted into the hole 20.

The container 12 is constructed of a material chosen from the group of materials consisting of copper, glass, and plastic. The container 12 has a height. The height is between about 2 inches and about 4 inches. The container 12 has a width, the width is between about 4 inches and about 6 inches.

A holding member 18 positioned in the interior space 16. The holding member 18 is comprised of scented wax 28 such that the stick of incense 22 facilitates an aroma is emitted from the holding member 18 when the stick of incense 22 melts the scented wax 28.

In use, the present invention would consist of a container designed to hold candle wax. A stick of incense would be located in the center of the wax. While burning, any ashes from the incense stick would fall into the bowl below. An agreeable scent would then be distributed throughout the home.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An incense burning assembly comprising:

a stick of incense;

a container, said container having an outer perimeter defining an interior space;

a holding member positioned in said interior space, said holding member being structured to include a hole, said hole receiving a portion of said stick of incense; and said holding member being comprised of scented wax such that said stick of incense facilitates an aroma being emitted from said holding member when said stick of incense burns down to said portion of said stick of incense received in said hole and heat from said stick of incense melts said scented wax.

2. The incense burning assembly of claim 1, further comprising:

said hole being positioned proximate a center of said holding member such that the stick of incense is positioned in a substantially central position relative to said container.

3. The incense burning assembly of claim 1, further comprising:

said hole being formed by a perimeter wall, said perimeter wall being substantially vertically oriented when said container is positioned on a support surface whereby said stick of incense is held in a substantially vertical orientation when inserted into said hole.

4. The incense burning assembly of claim 1, further comprising:

said container being constructed of a material chosen from the group of materials consisting of copper, glass, and plastic.

5. The incense burning assembly of claim 1, further comprising:

said container having a height, said height being between about 2 inches and about 4 inches, said container having a width, said width being between about 4 inches and about 6 inches.

6. An incense burning assembly comprising:

a stick of incense;

a container, said container having an outer perimeter defining an interior space;

a holding member positioned in said interior space, said holding member being structured to include a hole, said hole receiving a portion of said stick of incense;

said hole being positioned proximate a center of said holding member such that the stick of incense is positioned in a substantially central position relative to said container;

said hole being formed by a perimeter wall, said perimeter wall being substantially vertically oriented when said container is positioned on a support surface whereby said stick of incense is held in a substantially vertical orientation when inserted into said hole;

said container being constructed of a material chosen from the group of materials consisting of copper, glass, and plastic;

said container having a height, said height being between about 2 inches and about 4 inches, said container having a width, said width being between about 4 inches and about 6 inches; and said holding member being comprised of scented wax such that said stick of incense facilitates an aroma being emitted from said holding member when said stick of incense burns down to said portion of said stick of incense received by said hole and heat from said stick of scented wax.

* * * * *